United States Patent [19]

Berger et al.

[11] 4,139,546
[45] Feb. 13, 1979

[54] ANIONIC SILICONE DEFOAMER

[75] Inventors: Paul D. Berger; Tomas J. Benavides, both of Missouri City, Tex.

[73] Assignee: Witco Chemical Corporation, New York, N.Y.

[21] Appl. No.: 830,552

[22] Filed: Sep. 6, 1977

[51] Int. Cl.² ............................................. C07F 7/08
[52] U.S. Cl. ............................ 260/448.2 E; 252/171; 252/142; 252/156; 252/356; 260/448.2 B
[58] Field of Search .................. 260/448.2 B, 448.2 E; 252/171, 356

[56] References Cited

U.S. PATENT DOCUMENTS

| | | | |
|---|---|---|---|
| 3,047,497 | 7/1962 | Bluestein | 260/448.2 B X |
| 3,198,820 | 8/1965 | Pines et al. | 260/448.2B |
| 3,227,579 | 1/1966 | Bluestein | 260/448.2 B X |
| 3,248,409 | 4/1966 | Bluestein | 260/448.2 B X |
| 3,265,623 | 8/1966 | Pines et al. | 260/448.2 B X |

*Primary Examiner*—Paul F. Shaver
*Attorney, Agent, or Firm*—Albert L. Gazzola; Morton Friedman

[57] ABSTRACT

An anionic silicone defoamer having the following general formula:

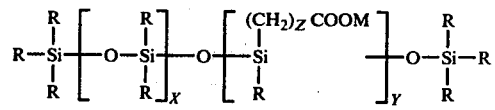

wherein:
R is alkyl;
X is 1 to 20;
Y is 1 to 10;
Z is 2 to 4, and;
M is a monovalent cation.

The anionic silicone defoamer is made, for instance, by reacting dimethyldichlorosilane, trimethylchlorosilane, and beta-cyanoethyl methyldichlorosilane in the presence of aqueous sodium hydroxide. Dry detergent compositions containing the present anionic silicone composition exhibit reduced foaming, even after several months of storage.

6 Claims, No Drawings

ANIONIC SILICONE DEFOAMER

This invention relates to anti-foaming agents and more particularly to novel anionic silicone defoamers useful in agricultural and detergent compositions. Specifically, the present invention relates to the incorporation of certain siloxanes as foam inhibitors in detergent formulations to reduce the foaming tendency of such formulations in water.

The present compositions are also useful in liquid hydrocarbons, particularly low vapor pressure fuels used as power fuels which have a tendency to foam when agitated in the presence of air or gases. Heretofore, various conventional anti-foam agents, such as polyglycols and morpholine as well as other organopolysiloxanes have been used in hydrocarbons with varying degrees of success.

In Bluestein et al., U.S. Pat. No. 2,992,083, granted on July 11, 1961, it is proposed to provide certain cyanoalkyl polysiloxanes as effective foam inhibitors particularly for low vapor pressure hydrocarbon fuels. Bluestein et al. utilized only cyano polymeric compositions with no reference or suggestion to the use of the present alkali polysiloxanes in detergent formulations or in hydrocarbon power fuels.

In Farminer et al., U.S. Pat. No. 3,843,558, granted on Oct. 22, 1974, it is proposed to coat sodium tripolyphosphate with an organopolysiloxane. There is no suggestion of an alkaline form of any polysiloxane as an anionic defoamer.

Nitzche et al., in U.S. Pat. No. 3,235,509, granted Feb. 15, 1966, propose trimethylsiloxy end-blocked polysiloxanes as effective anti-foaming agents in aqueous alkaline systems.

In U.S. Pat. No. 3,650,401, granted on Feb. 2, 1971 to O'Hara et al., anti-foaming agents are disclosed which are effective in aqueous media. These agents are formed from a polysiloxane, an inorganic oxide, and a basic material.

While the prior art anti-foam agents are to some degree effective, a satisfactory defoamer which is stable and effective in the presence of large amounts of nonionic and/or anionic surfactants, such as found in detergent laundry solutions, was not available before this invention was made.

It is therefore an object of this invention to provide an improved anionic silicone defoamer and a novel method for making same.

It is another object of this invention to provide an anionic silicone defoamer as aforesaid wherein the defoamer is prepared and used in the alkaline form of the silicone.

It is another object of this invention to provide an anionic silicone defoamer as aforesaid in an effective one-step reaction.

It is still another object of this invention to provide an anionic silicone defoamer as aforesaid wherein the defoamer retains its stability in the presence of large amounts of nonionic and/or anionic surfactants.

It is still another object of this invention to provide an anionic silicone defoamer as aforesaid which is useful in detergent formulations.

Broadly stated the defoamer of the present invention may be represented by the following Formula I:

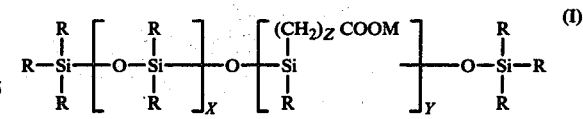

wherein:
R is alkyl, preferably methyl and/or ethyl;
X is 1 to 20;
Y is 1 to 10;
Z is 2 to 4; and
M is a monovalent cation such as ammonium or an alkali metal, the latter being preferred.

The method of preparing the defoamer of the present invention may be broadly stated as reacting a dialkyldihalosilane, trialkylhalosilane, and a beta-cyanoalkyl alkyldihalosilane in the presence of a hydroxide; such as sodium, potassium, lithium, or ammonium hydroxide.

Chlorosilanes are generally preferred, dimethyldichlorosilane and trimethylchlorosilane are commercially available, and are particularly preferred. The beta-cyanoalkyl alkyldichlorosilane may be prepared as disclosed in U.S. Pat. No. 2,922,083, granted July 11, 1961; U.S. Pat. No. 2,860,153, granted Nov. 11, 1958; and U.S. Pat. No. 2,837,551, granted June 3, 1958.

The preferred preparation of reaction ingredients to make the product of the present invention is as follows:

| Reactant | Approximate Weight Range | Approximate Moles |
|---|---|---|
| Dimethyldichlorosilane | 65–130 gm | 0.5–1.0 |
| Trimethylchlorosilane | 22 gm | 0.2 |
| Beta-cyanoethylmethyldichlorosilane | 19–60 gm | 0.1–0.3 |
| Sodium Hydroxide (40% Wt. Aqueous) Solution) | 150–310 gm (of solution) | 1.5–3.0 |

In a preferred embodiment in Formula I, X is 5 to 10, Y is 1 to 3, and Z is 2 or 3.

The anionic defoamer of the present invention may be employed in commercial preparations where foaming is a problem, such as in herbicides, detergents and cleansers, adhesives, cutting oils and lubricants, textile dyes, latex paints, and fuel oils.

Suitable detergents useful pursuant to the present invention include the sulfonates and phosphates, and particularly the linear alkyl benzene sulfonates. A concentration of anionic silicone defoamer of up to about 1% by weight of the detergent composition is generally sufficient to produce the desired effect.

Generally, it is desirable to use the present anionic silicone defoamers in concentrations of about 0.1 to 0.5 percent by weight. The specific proportion to be used being determined by the artisan in each particular instance. The anionic silicone defoamers of the present invention remain stable in dry detergent compositions even after several months of storage.

EXAMPLE I

First, 129 grams (i.e. 1 mole) of dimethyldichlorosilane are mixed with 38.6 grams (i.e. 0.2 moles) of betacyanoethylmethyldichlorosilane.

Then, 290 grams of a 40% aqueous solution of sodium hydroxide is added dropwise over a 30 minute period at room temperature to the above mixture, followed by 21.6 grams of trimethylchlorosilane.

The entire mixture is stirred and allowed to react for one hour and the product is allowed to separate from the salt water phase formed during the reaction.

A yield of 88% of a colorless oily liquid product is obtained.

EXAMPLE II

This example demonstrates the use of the present invention as a defoamer in detergent compositions.

Forty grams of the product obtained from Example I is absorbed on 25 grams of powdered silica. Then 0.162 grams of this absorbed product is added to 100 grams of a commercial heavy duty laundry detergent. A 5 percent solution of this detergent mixture in water at 120° F. gives no foam when agitated in a Hobart mixer for thirty minutes. This detergent solution without the antifoamer from Example I, foams over in less than 5 minutes.

The foregoing dry detergent formulation containing the anti-foamer of the Example I remains stable and effective after shelf storage for over three months.

The embodiments of the invention in which an exclusive property or privilege is claimed are defined as follows:

1. A method for preparing an anionic silicone defoamer having the following formula:

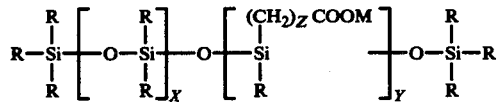

wherein:
R is alkyl;
X is 1 to 20;
Y is 1 to 10;
Z is 2 to 4, and;
M is a monovalent cation;
said method comprising:
Reacting dialkyldihalosilane, trialkylhalosilane and beta-cyanoethyl or beta-cyanopropyl alkyldihalosilane in the presence of MOH, wherein M is as aforesaid and wherein the alkyl of the silane is $CH_3$ or $C_2H_5$.

2. The method of claim 1, wherein M is an alkali metal.

3. The method of claim 1, wherein M is sodium.

4. The method of claim 1, wherein the R is methyl.

5. A laundry detergent composition comprising a detergent selected from a sulfonate and a phosphate and up to about 1% by weight of an anionic silicone defoamer having the following general formula:

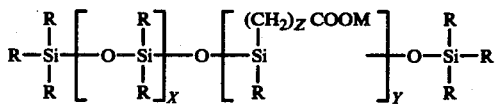

wherein:
R is alkyl;
X is 1 to 20;
Y is 1 to 10;
Z is 2 to 4, and;
M is a monovalent cation.

6. The laundry detergent of claim 5, wherein the sulfonate is a linear alkyl benzene sulfonate.

* * * * *